United States Patent
Hassler et al.

(10) Patent No.: US 10,420,650 B2
(45) Date of Patent: Sep. 24, 2019

(54) INTERPOSITION IMPLANTS FOR THE HAND

(71) Applicant: TORNIER, Montbonnot-Saint-Martin (FR)

(72) Inventors: Michel Hassler, Saint Ismier (FR); Philippe Bellemere, Nantes (FR)

(73) Assignee: TORNIER, Montbonnot-Saint-Martin (FR)

( * ) Notice: Subject to any disclaimer, the term of this patent is extended or adjusted under 35 U.S.C. 154(b) by 67 days.

(21) Appl. No.: 15/401,812

(22) Filed: Jan. 9, 2017

(65) Prior Publication Data

US 2017/0172753 A1 Jun. 22, 2017

Related U.S. Application Data

(63) Continuation of application No. 13/943,647, filed on Jul. 16, 2013, now Pat. No. 9,572,673, which is a (Continued)

(30) Foreign Application Priority Data

| Jun. 19, 2009 | (FR) | ..................................... 09 54190 |
| Jul. 16, 2012 | (FR) | ..................................... 12 56863 |

(51) Int. Cl.
| A61F 2/42 | (2006.01) |
| A61F 2/30 | (2006.01) |
| A61F 2/38 | (2006.01) |

(52) U.S. Cl.
CPC ........ *A61F 2/4241* (2013.01); *A61F 2/30721* (2013.01); *A61F 2/4261* (2013.01); (Continued)

(58) Field of Classification Search
CPC ............ A61F 2/4241; A61F 2002/4258; A61F 2002/4276
See application file for complete search history.

(56) References Cited

U.S. PATENT DOCUMENTS

| 4,936,860 A | 6/1990 | Swanson |
| 5,314,486 A | 5/1994 | Zang et al. |
| (Continued) | | |

FOREIGN PATENT DOCUMENTS

| DE | 101 30 796 | 1/2003 |
| EP | 1 508 316 | 2/2005 |
| (Continued) | | |

OTHER PUBLICATIONS

European Search Report issued in European Patent Application No. 10166447, dated Oct. 25, 2010, in 4 pages.

(Continued)

*Primary Examiner* — Bruce E Snow
*Assistant Examiner* — Melissa A Hoban
(74) *Attorney, Agent, or Firm* — Knobbe, Martens, Olson & Bear LLP

(57) ABSTRACT

An implant couples a first bone of a hand to a second bone of the hand. The implant includes a body that defines a median plane. The body also defines a first joint surface having a first central region that articulates with the first bone. The body further defines a second joint surface having a second central region that articulates with the second bone, and the second central region is disposed on an opposite side of the median plane of the body relative to the first central region. The first and second central regions correspond to profiles of first and second axial segments, respectively, the first and second axial segments are each one of a cylinder, a cone and a torus and are centered on first and second axes, respectively, and the first and second axes, as projected on the median plane, are substantially perpendicular to each other.

17 Claims, 11 Drawing Sheets

Related U.S. Application Data continuation-in-part of application No. 12/819,390, filed on Jun. 21, 2010, now Pat. No. 9,408,706.

(60) Provisional application No. 61/706,584, filed on Sep. 27, 2012, provisional application No. 61/674,089, filed on Jul. 20, 2012.

(52) U.S. Cl.
CPC ......... *A61F 2/30724* (2013.01); *A61F 2/3872* (2013.01); *A61F 2002/302* (2013.01); *A61F 2002/30113* (2013.01); *A61F 2002/30153* (2013.01); *A61F 2002/30204* (2013.01); *A61F 2002/30205* (2013.01); *A61F 2002/30224* (2013.01); *A61F 2002/30301* (2013.01); *A61F 2002/30616* (2013.01); *A61F 2002/30754* (2013.01); *A61F 2002/4258* (2013.01); *A61F 2230/0019* (2013.01); *A61F 2230/0065* (2013.01); *A61F 2230/0067* (2013.01); *A61F 2230/0069* (2013.01); *A61F 2230/0095* (2013.01); *A61F 2310/00173* (2013.01); *A61F 2310/00574* (2013.01)

(56) References Cited

U.S. PATENT DOCUMENTS

| | | | |
|---|---|---|---|
| 5,326,364 | A | 7/1994 | Clift et al. |
| 5,425,777 | A | 6/1995 | Sarkisian et al. |
| 5,549,690 | A | 8/1996 | Hollister et al. |
| 5,683,466 | A | 11/1997 | Vitale |
| 5,702,472 | A | 12/1997 | Huebner |
| 6,017,366 | A | 1/2000 | Berman |
| 6,436,146 | B1 | 8/2002 | Hassler et al. |
| 8,012,217 | B2 | 9/2011 | Strzepa et al. |
| 8,292,954 | B2 * | 10/2012 | Robinson ............ A61F 2/4606 623/14.12 |
| 2005/0113926 | A1 | 5/2005 | Zucherman et al. |
| 2006/0241758 | A1 | 10/2006 | Peterman et al. |
| 2006/0241777 | A1 | 10/2006 | Partin et al. |
| 2006/0241778 | A1 | 10/2006 | Ogilvie |
| 2007/0123993 | A1 | 5/2007 | Hassler et al. |
| 2008/0051912 | A1 | 2/2008 | Hollawell |
| 2009/0254190 | A1 | 10/2009 | Gannoe et al. |
| 2010/0057216 | A1 | 3/2010 | Graham |
| 2010/0249942 | A1 | 9/2010 | Goswami et al. |
| 2012/0158153 | A1 * | 6/2012 | Hardenbrook ........ A61F 2/4261 623/21.12 |

FOREIGN PATENT DOCUMENTS

| | | |
|---|---|---|
| EP | 1 637 095 | 3/2006 |
| EP | 2 263 614 | 1/2010 |
| FR | 2 465 470 | 3/1981 |
| FR | 2 709 948 | 3/1995 |
| FR | 2 957 780 | 9/2011 |
| WO | WO 1997/042895 | 11/1997 |
| WO | WO 1998/047449 | 10/1998 |
| WO | WO 2004/093767 | 11/2004 |
| WO | WO 2006/000890 | 1/2006 |

OTHER PUBLICATIONS

French Preliminary Search Report issued in French Patent Application No. 0954190, completed Feb. 23, 2010, in 6 pages.

French Search Report and Written Opinion issued in French Application No. 1152587, dated Oct. 24, 2011 in 5 pages.

French Search Report issued in French Patent Application No. 0954190, dated Apr. 13, 2011, in 2 pages.

French Search Report issued in French Patent Application No. 1256863, dated Mar. 28, 2013, in 2 pages.

\* cited by examiner

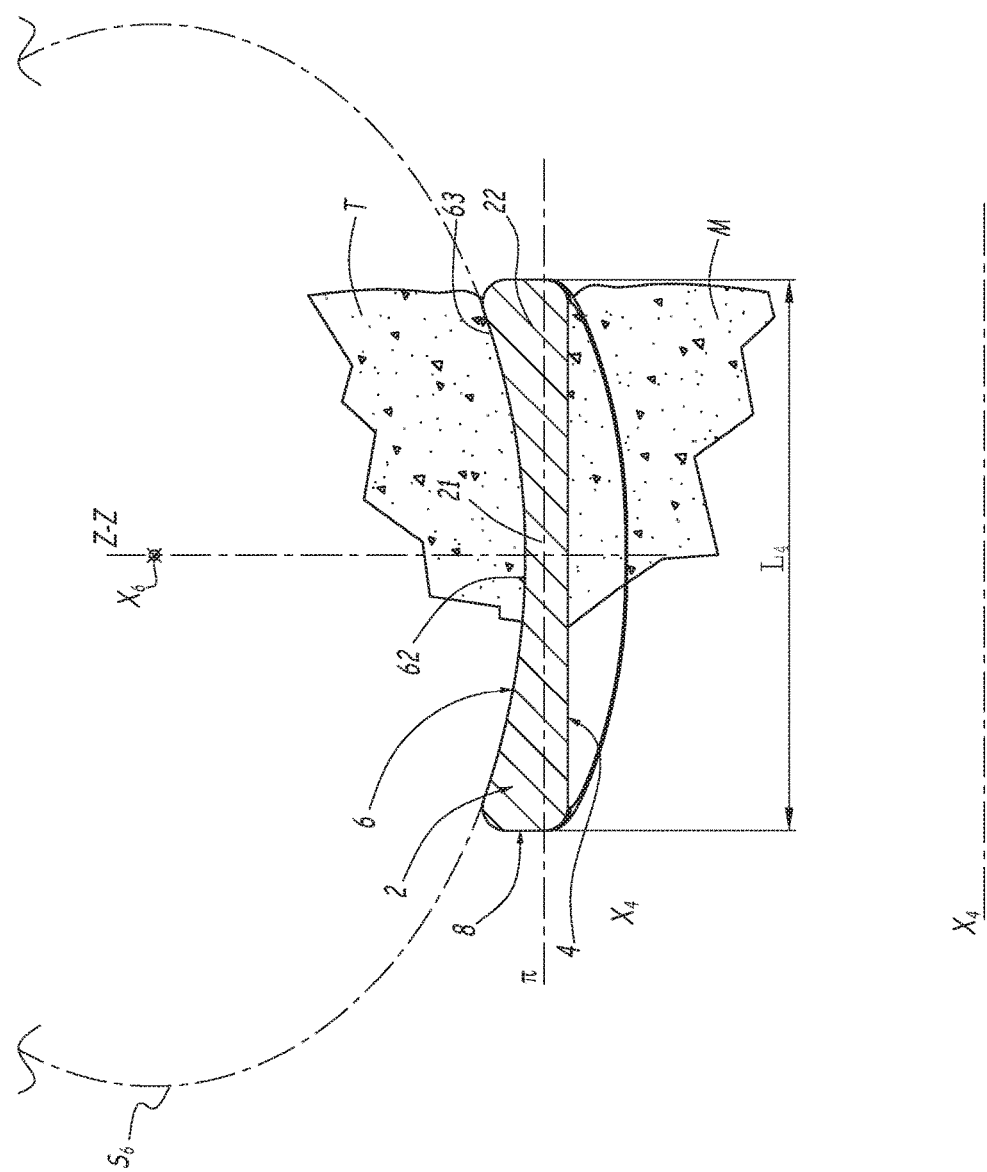

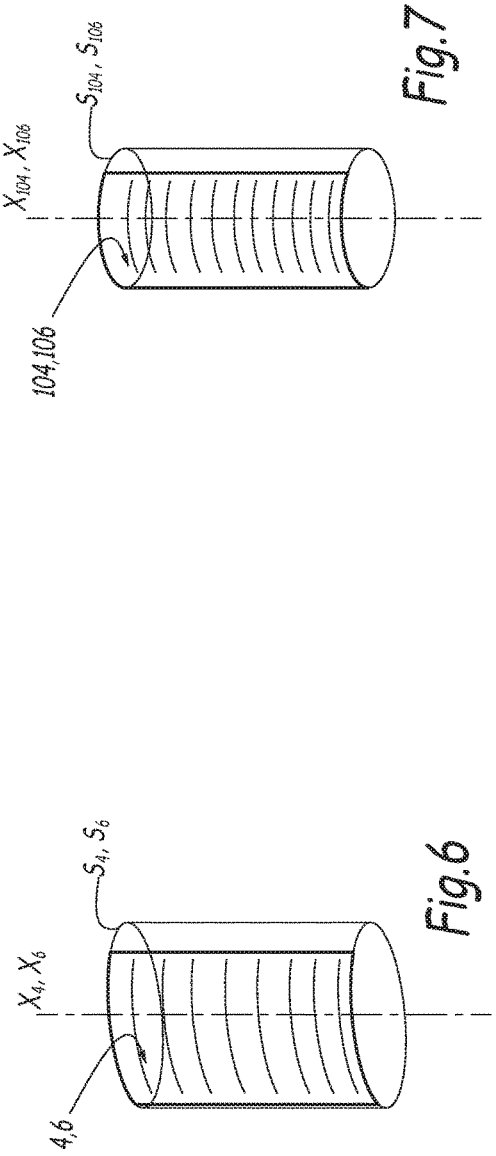

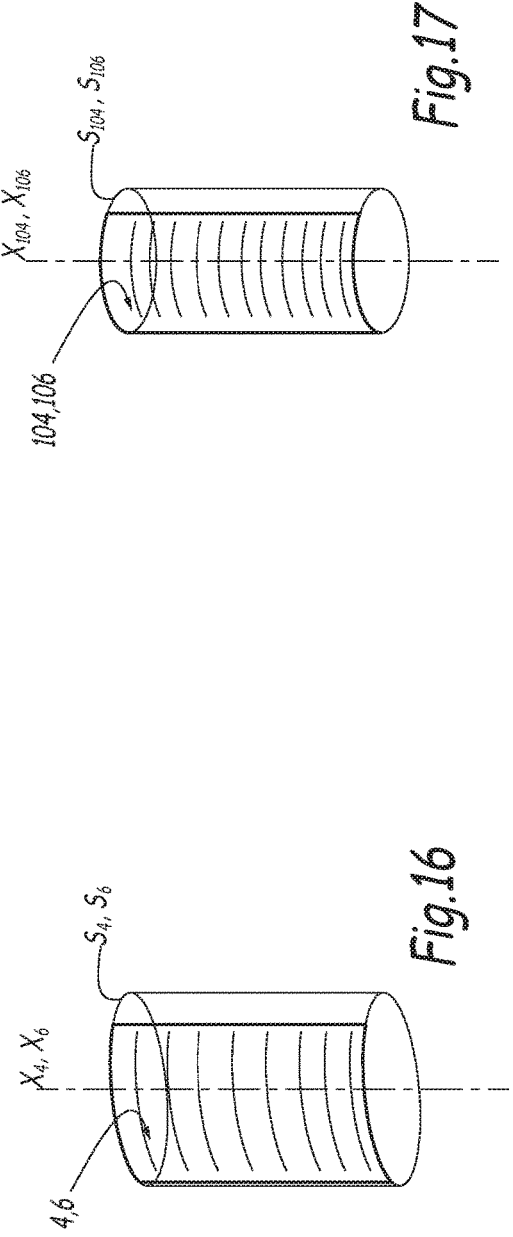

INTERPOSITION IMPLANTS FOR THE HAND

CROSS-REFERENCE TO RELATED APPLICATION

The present application is a continuation of U.S. application Ser. No. 13/943,647 filed Jul. 16, 2013, entitled "INTERPOSITION IMPLANTS FOR THE HAND," which is a continuation-in-part application of U.S. patent application Ser. No. 12/819,390 filed Jun. 21, 2010, entitled "TRAPEZIOMETACARPAL JOINT IMPLANT AND ASSOCIATED METHODS," which claims the benefit of French Patent Application No. FR0954190, filed on Jun. 19, 2009, and entitled "IMPLANT D'ARTICULATION TRAPEZO-METACARPIENNE," French Patent Application No. FR1256863, filed on Jul. 16, 2012, and entitled "IMPLANT D'INTERPOSITION TRAPEZIEN," U.S. Provisional Application Ser. No. 61/674,089, filed Jul. 20, 2012, and entitled "IMPLANT D'INTERPOSITION TRAPEZIEN," and U.S. Provisional Application Ser. No. 61/706,584, filed Sep. 27, 2012, and entitled "TRAPEZIO-METACARPAL JOINT IMPLANT." The disclosures of the above applications are incorporated herein by reference in their entireties for all purposes.

BACKGROUND

Trapeziometacarpal prostheses and implants are designed to restore the strength and mobility of the anatomical joint of the thumb, between its metacarpal and the trapezium, when the joint is damaged by a degenerative or inflammatory pathological process. Many trapeziometacarpal prostheses are stem prostheses in which the metacarpal prosthetic component is anchored at one end in the metacarpal by an elongate stem while the other end of the prosthetic component is mounted pivotably either in a prosthetic component attached to the trapezium or in a cavity hollowed out in the trapezium. The implantation of these total or partial prostheses requires considerable cutting of the bone substance of the trapeziometacarpal joint and restores a ball-and-socket type of mobility which, from the point of view of kinematics, does not correspond to the mobility of the anatomical joint. Moreover, in the event of poor implantation, there are real risks of wear, luxation, or even prosthesis fracture. Some trapeziometacarpal implants without stems have also been proposed, those implants being implanted into a cavity or cavities formed in the trapezium and/or metacarpal. Often times, because of the compressive stresses applied to the implant body by the surrounding ligaments of the joint, the implant body gradually engages deeper in the bones, reducing the space between the bones and, consequently, their relative mobility.

Total trapeziectomy may be performed based on indications of, for example, peritrapezial arthritis, that is, arthritis affecting the different joint surfaces of the trapezium, and isolated arthritis, such as arthritis of the trapeziometacarpal joint, also called rhizarthrosis. Trapeziectomy allows the first metacarpal to articulate in the space that was previously occupied by the trapezium. However, if no movement is associated therewith (e.g. the muscles are weakened or not able to provide sufficient forces), the column of the palm of the hand retracts due to ligament tension. As such, the ligament tension collapses the space that was previously occupied by the trapezium, prevents articulation of the first metacarpal, and causes pain due to secondary arthritis. As such, the total trapeziectomy is typically only employed together with ligamentoplasty. That is, a structure that is formed from, for example, a ligament taken from the patient or synthetic fibers is implanted in the space that was previously occupied by the trapezium to inhibit the base of the thumb from descending. However, the results of such ligamentoplasties are typically poor. In particular, such ligamentoplasties are typically associated with a very long functional recovery period, awkward shortening of the column of the thumb with hyperextension compensating the metacarpophalangeal joint, decreased gripping strength of the thumb, and long-term deterioration of the structure due to a metacarpotrapezial and/or metacarpal scaphoid conflict, which is in turn due to the shortening of the trapezium cavity.

Previously, trapezium interposition implants were proposed to address the issues described above. Some trapezium implants typically include a single-piece silicon body having a cylindrical part to replace the trapezium, a concave end to engage the scaphoid, and an opposite end having a conical stabilizing tail to be inserted into the metacarpal. Unfortunately, these interposition implants typically cause one or more problems, such as silicon debris causing "siliconites" with significant bone resorption, implant fracture, and/or implant instability.

Other trapezium implants are designed to replicate the natural trapezium bone. However, these implants also cause one or more problems. For example, when a trapeziectomy is performed, arthritis has typically advanced to a degree that the tissues surrounding the trapezium are significantly deformed. As such, it may be difficult to stably position such implants. Furthermore, if stabilizing means are attached to these implants, they are particularly painful for patients due to the excess stresses they cause in the hand.

Another type of trapezium interposition implant includes a spherical or ellipsoid single-piece body that is placed in the trapezium cavity. This implant addressed the issues of retraction of the column of the thumb and the recovery period related for trapeziectomy. However, given its convex shape, this implant must be placed using a delicate surgical technique based on medialization of the implant. Specifically, the implant must be pushed into a "cul-de-sac" prepared by the surgeon by partial resection of the trapezoid facilitate implant stability.

SUMMARY

Some embodiments relate to a trapeziometacarpal implant that is permanently or semi-permanently implantable and provides mobility more similar to natural, anatomical mobility of the trapeziometacarpal joint. The trapeziometacarpal joint implant includes a body defining a metacarpal joint surface and a trapezium joint surface that are situated, at least in their central region, on either side of a median plane of the body. Each of the metacarpal and the trapezium joint surfaces correspond to a profile of an axial segment of a cylinder, a cone, or a torus, the axial segments of the cylinder, cone and/or torus being centered on respective axes which, as projected on the median plane, are substantially perpendicular to each other.

Some embodiments relate to a surgical method for fitting a trapeziometacarpal joint implant in which an articular area between the metacarpal and trapezium of a patient is accessed, the cortical bone surface of the trapezium is prepared so as to substantially match the trapezium joint surface defined by a body of an implant and, if need be, the cortical bone surface of the metacarpal is prepared so as to substantially match a metacarpal joint surface defined by the body of the implant, and the body of the implant is interposed between the trapezium and the metacarpal in such a way that an axis associated with the trapezium joint surface extends in either the antero-posterior or frontal plane of the patient, while an axis associated with the metacarpal joint surface extends in the other of the antero-posterior or front planes.

Some embodiments relate to interposing between the trapezium and the metacarpal a relatively thin body (e.g., as opposed to a body that is voluminous and spherical or ellipsoid) with opposite joint surfaces which are concave at least in one direction and against which the cortical bone surfaces of the trapezium and of the metacarpal come to bear so as to roll and slide thereon. In order to reproduce the anatomical behavior of the saddle-type trapeziometacarpal joint, the two joint surfaces correspond to profiles of axial segments of a cylinder, cone and/or torus, of which the central axes or, more generally, taking account that the central axis of an axial segment of a torus is curved, the projections of these central axes on the median plane of the implant, are substantially perpendicular to each other.

In some embodiments, the body of the implant simulates the anatomical saddle-type trapeziometacarpal joint with the two joint surfaces. From the point of view of kinematics, the two, orthogonal joint surfaces of the implant body permit pivoting mobility about the two aforementioned central axes, in the manner of a cardan joint, or universal joint, to which the trapeziometacarpal joint is similar from a mechanical point of view. Moreover, the curvature of the two joint surfaces stabilizes and aligns the body of the implant between the trapezium bone and the metacarpal bone, thus avoiding the need to provide means of fixation to the bone(s). Moreover, by maximizing an area of contact between the implant and the bones of the trapezium and metacarpal in the area of the two joint surfaces, the implant body is adapted to reduce the likelihood of being forced into the bones, thereby retaining mobility of the joint.

In some embodiments, the body of the implant is minimized in thickness, where a range of thicknesses are optionally offered to a surgeon during implantation depending on a degree of wear of the joint that is being treated. Generally, the natural contours of the trapezium and metacarpal cortical bone surfaces are well-matched for cooperating with the joint surfaces of the implant. In cases of substantial wear, however, minimizing thickness of the implant helps minimize an amount of bone cutting required to match the mutually facing cortical bone surfaces of the trapezium and of the metacarpal to the joint surfaces of the body of the implant. In turn, for some trapeziometacarpal joints that are not greatly damaged, resection of the metacarpal can be minimal or even unnecessary. Typically, the size of the implant is selected such that the implant body is stabilized by the stress provided by the capsular and ligament envelope around the joint between the trapezium and the metacarpal, without the implant body being overstressed. For example, in some embodiments, the implant body retains a certain degree of freedom of movement to help the implant adjust its position, or adapt, as a function of the stresses of the articular envelope associated with the various possible movements of the trapeziometacarpal joint.

Various embodiments relate to a trapeziometacarpal joint implant having a trapezium joint surface and a metacarpal joint surface opposite the trapezium joint surface. In some embodiments, one or both of the metacarpal and trapezium joint surfaces correspond to a profile of an axial segment of a cylinder, a cone, or a torus having a cross section that is curved, curved inward along its entire periphery, elliptic, and/or circular. In some embodiments, the cross section associated with the metacarpal and/or trapezium joint surface has, in the central region of the joint surface, a smaller curvature than a remainder of the cross section and, if desired, in the peripheral region of the joint surface, a greater curvature than a remainder of the cross section. The metacarpal and trapezium joint surfaces are separated from each other, in a direction perpendicular to a median plane of the implant, by a maximum thickness of the body of less than 5 mm, according to some embodiments. The trapezium joint surface optionally has a dimension, along its associated axis, greater than the dimension of the metacarpal joint surface along its associated axis. In some embodiments, the body is without any means of fixation to bone and the implant body is formed as a single, unitary component.

In some embodiments, an implant is adapted to couple a first bone of a hand of a subject to a second bone of the hand of the subject. The implant includes a body that defines a median plane. The body also defines a first joint surface having a first central region adapted to articulate with the first bone. The body further defines a second joint surface having a second central region adapted to articulate with the second bone, and the second central region is disposed on an opposite side of the median plane of the body relative to the first central region. The first central region and the second central region correspond to profiles of a first axial segment and a second axial segment, respectively, the first and second axial segments are each one of a cylinder, a cone and a torus and are centered on a first axis and a second axis, respectively, and the first and second axes, as projected on the median plane, are substantially perpendicular to each other.

In some embodiments, an interposition implant is adapted to couple a first metacarpal of a hand of a subject to a second bone of the hand of the subject. The implant includes a body that defines a median plane. The body includes a first metacarpal joint surface that has a first central region adapted to articulate with the first metacarpal. The body further includes a second joint surface that has a second central region adapted to articulate with the second bone. The second central region is disposed on an opposite side of the median plane of the body relative to the first central region. The first central region and the second central region correspond to profiles of a first axial segment and a second axial segment, respectively. The first and second axial segments are each one of a cylinder, a cone and a torus and are centered on a first axis and a second axis, respectively. The first and second axes, as projected on the median plane, are substantially perpendicular to each other.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 4 and 5 are sections along the lines IV-IV and V-V, respectively, from FIG. 3, also showing some of the bones of the hand after the implant of FIG. 1 has been positioned, according to some embodiments.

FIG. 6 is a diagram illustrating a design geometry of joint surfaces of the implant of FIG. 1, according to some embodiments.

FIGS. 7 to 9 are diagrams illustrating other design geometries of joint surfaces of other implants, according to some embodiments.

FIG. 16 is a diagram illustrating the construction geometry of the articular surfaces of the implant of FIGS. 10 to 15.

FIGS. 17 to 19 are views similar to FIG. 16, respectively illustrating alternatives for the construction geometry of the articular surfaces of the implant according to the invention.

Figure 1:
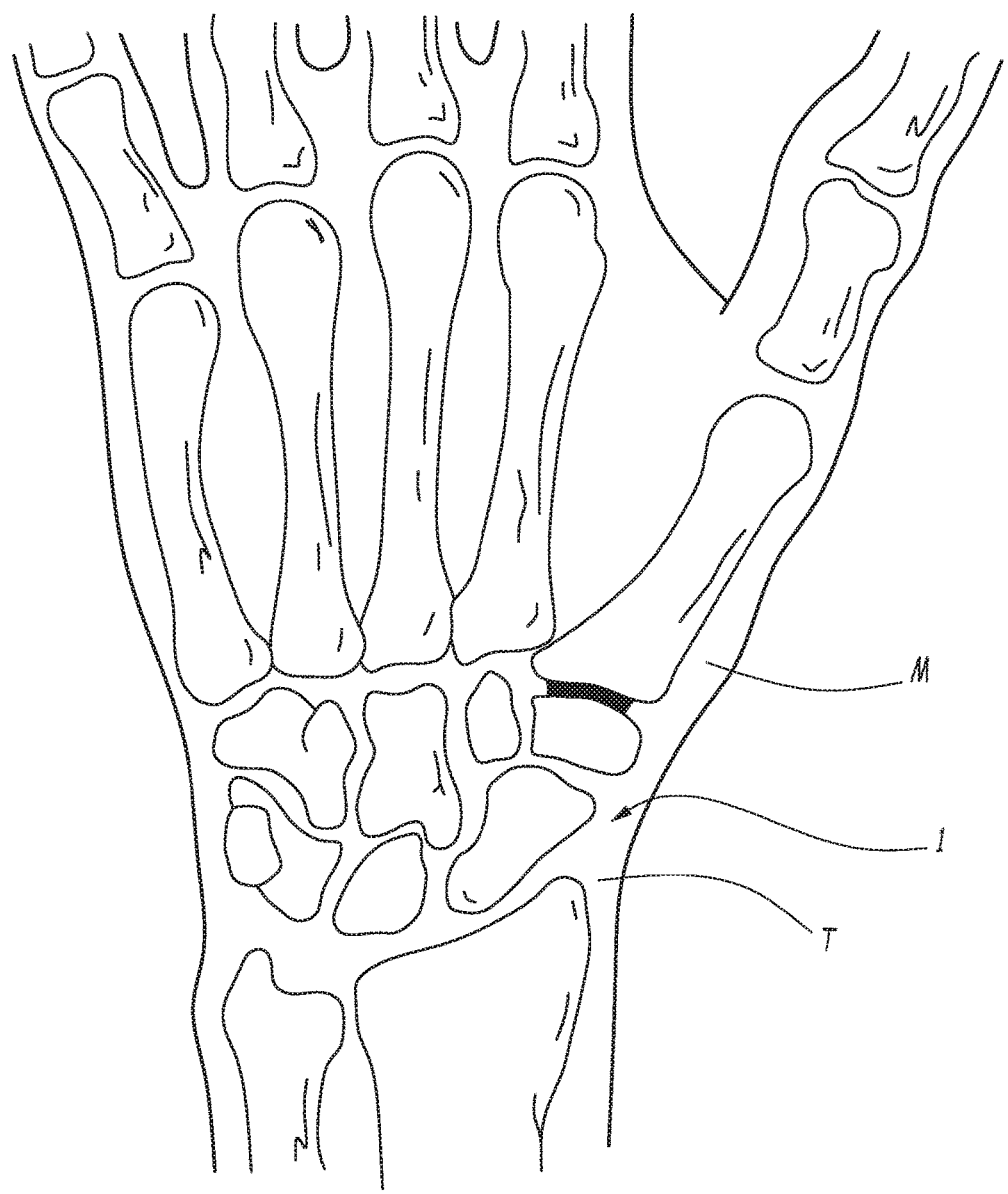
FIG. 1 is an elevation view showing an implant interposed between a trapezium and metacarpal of a human hand, according to some embodiments.
Figure 2:
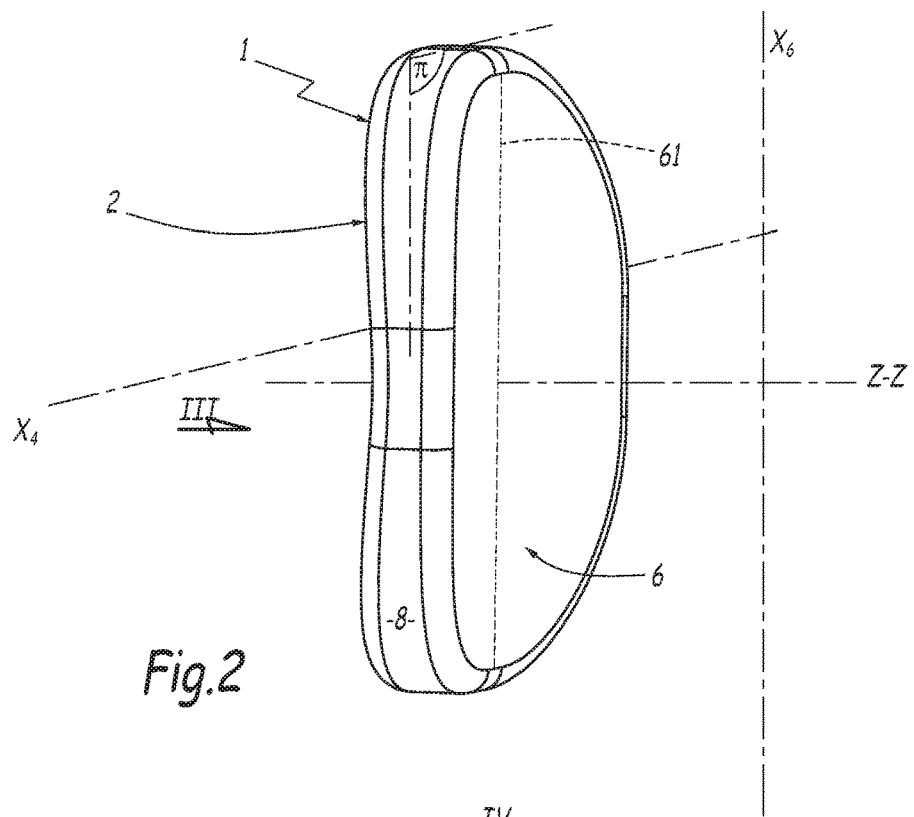
FIG. 2 is a perspective view of the implant of FIG. 1, according to some embodiments.
Figure 3:
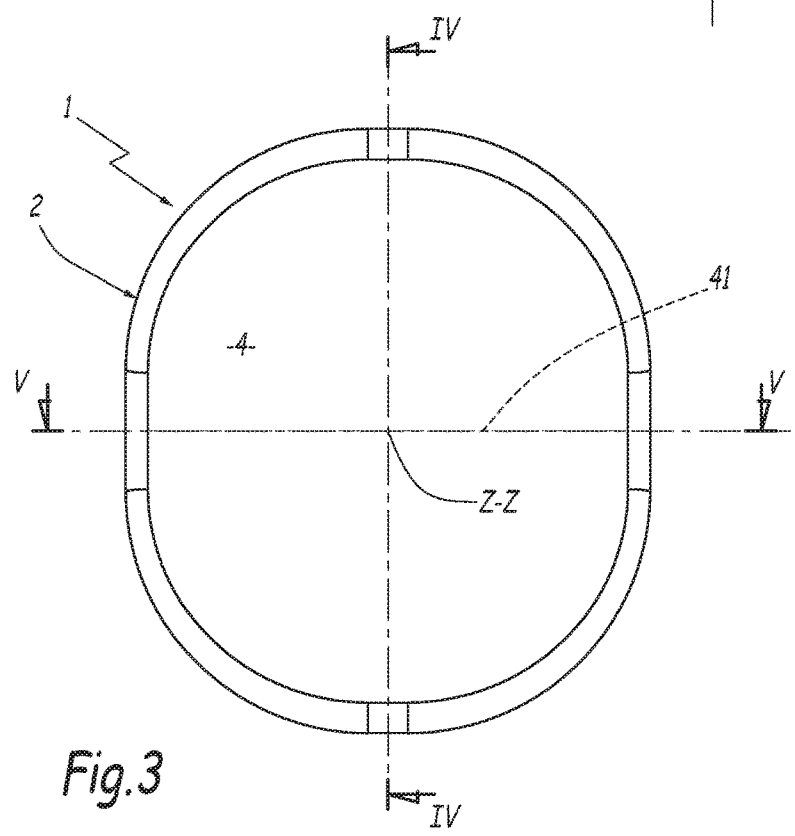
FIG. 3 is an elevation in the direction of the arrow III in FIG. 2, according to some embodiments.

While the invention is amenable to various modifications and alternative forms, specific embodiments have been shown by way of example in the drawings. The intention, however, is not to limit the invention to the particular embodiments depicted. On the contrary, the invention is intended to cover all modifications, permutations, equivalents, and alternatives falling within the scope of the invention as defined by the appended claims.

DETAILED DESCRIPTION

As used herein, the terms "frontal," "antero-posterior," and similar terms are to be understood in their anatomical sense in relation to a patient whose hand is being operated upon. With that in mind, in FIGS. 1 to 5, an embodiment of a trapeziometacarpal implant 1 according to the present invention is shown. The implant 1 is designed to be implanted by interposition in a trapeziometacarpal joint between a trapezium T and a first metacarpal M of a human hand, as is shown by way of example in FIG. 1.

The implant 1 comprises a generally disk-shaped body 2 centered on a geometric axis Z-Z, also described as a transverse axis. The body 2 delimits a first main surface 4 and a second main surface 6, also referred to as metacarpal and trapezium joint surfaces, respectively, or primary bone contact surfaces, for example. In some embodiments, the first and second main surfaces 4 and 6 are positioned opposite each other on the axis Z-Z and separated from each other by the thickness of the body 2 along the axis Z-Z. The body 2 also includes a peripheral surface 8 that connects the first and second main surfaces 4 and 6. In some embodiments, the generatrices of the peripheral surface 8 are parallel to the axis Z-Z.

As shown, the transverse profile of the body 2 is generally rectangular. In particular, in a cross section that is transverse to the axis Z-Z, the body 2 has a rectangular outer contour with rounded corners, although a variety of shapes are contemplated, including square, circular, elliptical, and others, for example.

As shown, the implant 1 is formed as a single, unitary piece, consisting of the body 2 without extraneous components, such as a bone fixation component (e.g., a screw) for anchoring the body 2 in the metacarpal M or in the trapezium T. For example, in some embodiments, the body 2 is secured in position via interposition between metacarpal M and the trapezium T such that the body retains some freedom of movement to adapt its position to the stresses applied to it as a function of movements of the trapeziometacarpal joint.

In some embodiments, the body 2 is formed as a single piece of graphite covered with a layer of pyrolytic carbon, which provides good biocompatibility, high mechanical strength, and resists wearing of the metacarpal and the trapezium. Although graphite and pyrolytic carbon have been referenced, other materials are contemplated, including metals such as chromium cobalt alloys and plastics, such as polyethylene, PEEK, silicone, as well as ceramics and others.

Figure 4:
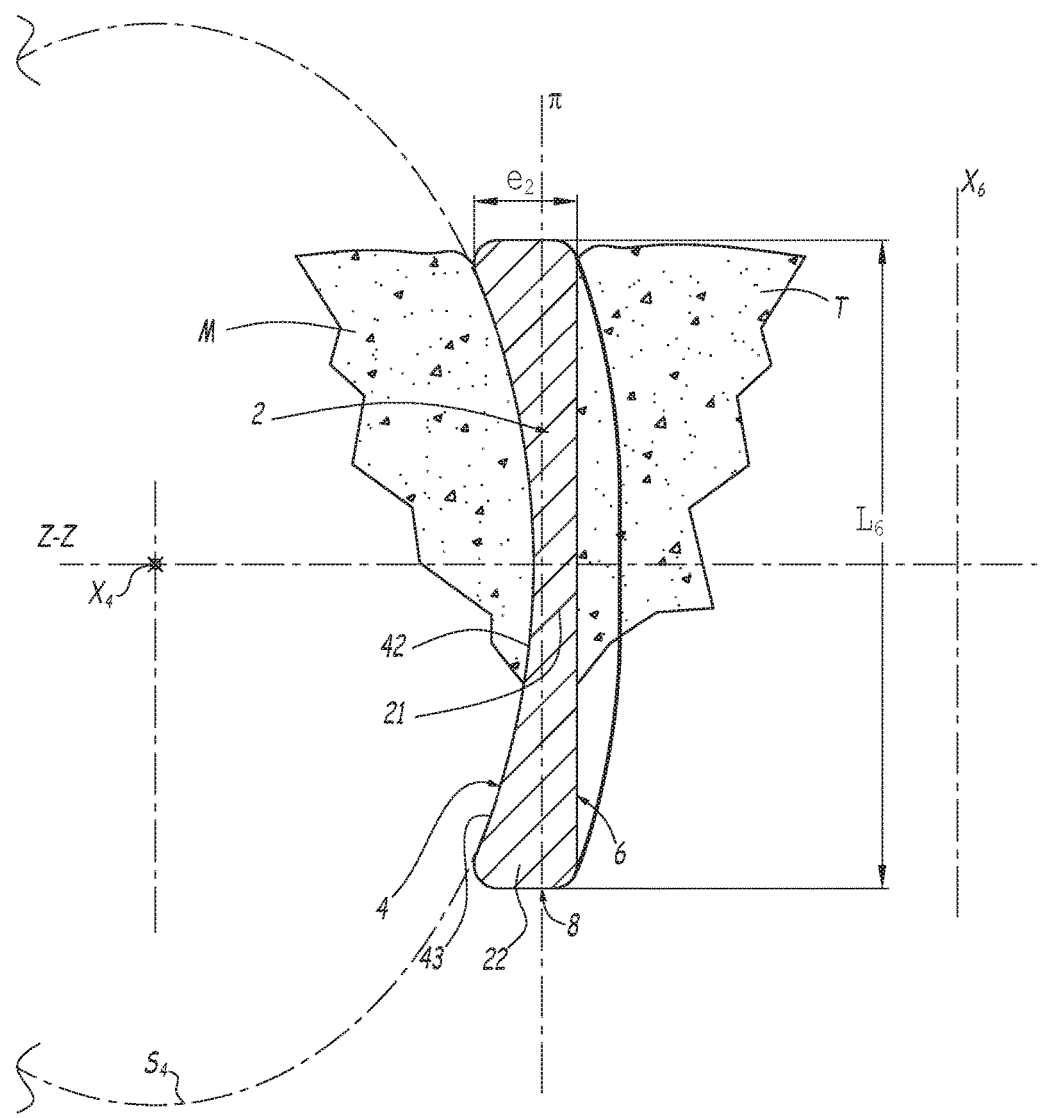

As shown in FIG. 4, the first main surface 4 is concave and corresponds geometrically to a profile of an axial segment of a cylinder portion which is centered on a first axis $X_4$ and defines a first cross section $S_4$ that is substantially elliptic. In some embodiments, the first cross section $S_4$ is constant along the first axis $X_4$ and corresponds to the directrix of the first main surface 4. As shown, the first axis $X_4$ extends perpendicular to the axis Z-Z, the axes $X_4$ and Z-Z intersecting with one another (for reference, the first axis $X_4$ extends in and out of the page as depicted in FIG. 4).

As shown in FIG. 5, the second main surface 6 is also concave and corresponds to a cylinder portion whose second cross section $S_6$ is substantially elliptic and which is centered on a second axis $X_6$ perpendicular to and intersecting the axis Z-Z (for reference, the axis $X_6$ extends in and out of the page as depicted in FIG. 5).

Thus, as shown, the axes $X_4$ and $X_6$ extend perpendicular to each other and do not intersect. Base lines 41 (FIG. 2) and 61 (FIG. 3) belong respectively to the first and second main surfaces 4 and 6. Each of the base lines 41 and 61 extend parallel to the axes $X_4$ and $X_6$ and are perpendicular to each other. The base lines 41 and 61 are separated, on the axis Z-Z, by a central part 21 of the body 2. In different terms, in a median plane π of the body 2, which is perpendicular to the axis Z-Z and on either side of which the first and second main surfaces 4 and 6 are situated, the respective projections of the axes $X_4$ and $X_6$ are perpendicular and secant.

In some embodiments, in cross section through the axis Z-Z, the body 2 has a variable thickness, the thickness being at its minimum in the central part 21 of the body and gradually increasing in the direction away from the central part 21 toward a peripheral part 22 of the body 2, as shown in FIGS. 4 and 5.

The following method of fitting the implant in place between the metacarpal M and the trapezium T is accordance with some embodiments and is provided by way of example. Thus, in some embodiments, a first operating step includes a surgeon accessing the articular area between the metacarpal M and the trapezium T via a posterior or antero-lateral approach. To access the interosseous space between the metacarpal and the trapezium, the articular capsule and the ligaments surrounding the articular area are either preserved, by being retracted, or are partially incised, it being understood that the capsule and its ligaments will then be reconstructed at the end of intervention.

In some embodiments, in a second operating step, the surgeon moves the metacarpal M and the trapezium T apart from each other in order to widen the interosseous space, in particular by applying a tensile force in the longitudinal direction of the metacarpal. The surgeon is then better able to prepare the bone surfaces delimited by the metacarpal M and the trapezium T, in such a way as to shape these surfaces so that they match the first and second main surfaces 4 and 6 of the body 2 of the implant 1.

In practice, it will be noted that the mutually facing ends of the metacarpal M and of the trapezium T have respective surface geometries that are close to surfaces matching the first and second main surfaces 4 and 6. This is because these bone ends, in their anatomical state, have saddle shapes, which fit orthogonally one into the other. Thus, the cuts made in the bone on the mutually facing ends of the metacarpal M and the trapezium T for adapting the surface of the bones M and T to the surfaces 4 and 6 of the body 2 can be minimal, according to some embodiments. In particular, the cuts are often minimal or even unnecessary on the metacarpal M, whereas more substantial cuts may have to be made on the trapezium T. In some embodiments, preparation of the ends of the metacarpal M and/or of the trapezium T does not require any deep cutting into the bones, as cutting remains confined to the cortical bone layer.

In some embodiments, in a third operating step, the tension applied to the trapeziometacarpal joint in the longitudinal direction of the metacarpal M is maintained. The surgeon positions the implant 1 in the interosseous space separating the metacarpal M and the trapezium T by interposing the body 2 between the two bones M and T in such a way that the first main surface 4 is directed toward the metacarpal M, with the first axis $X_4$ extending in a frontal plane, while the second main surface 6 is directed toward the trapezium T, with the second axis $X_6$ extending in an antero-posterior plane.

In a variant not shown, the implant 1 is fitted in place, between the metacarpal M and the trapezium T, in a configuration tilted by 90 degrees about the axis Z-Z. The ends of the metacarpal M and of the trapezium T are prepared in advance of fitting the implant 1, according to some embodiments. Regardless, the body 2 is optionally implanted in such a way that the first and second main surfaces 4 and 6 adapt better to the ends of the metacarpal M and trapezium T of the patient being operated on, depending on the initial state of these bone ends, and/or to minimize a depth to which the bone ends are cut during preparation.

Once the implant 1 has been positioned, or interposed, between the metacarpal M and the trapezium T, the axial tension applied to the trapeziometacarpal joint is released, such that the articular capsule and the ligaments surrounding the trapeziometacarpal joint move the metacarpal M and the trapezium T toward each other. In some embodiments, the body 2 of the implant 1 and/or the metacarpal M and trapezium T are adapted such that the implant 1 is held movably between the metacarpal M and the trapezium T, under the stress provided by the capsule and the ligaments. In other words, the capsule and the ligaments provide a stress whose resultant force, or a substantial component thereof, is substantially aligned with the axis Z-Z. The surgeon then closes the soft tissues around the trapeziometacarpal joint, if appropriate by reconstruction, or by ligamentoplasty, for example.

The trapeziometacarpal joint thus fitted with the implant 1 exhibits a kinematic behavior similar to, or even nearly identical to the natural anatomical behavior of the trapeziometacarpal joint. For example, the implant 1 is configured such that the metacarpal M articulates against the first main surface 4 by tilting about the first axis $X_4$ whereas the trapezium T concurrently articulates against the second main surface 6 by tilting about the second axis $X_6$. By virtue of the implant 1, the metacarpal M and the trapezium T are articulated with respect to each other in the manner of a cardan joint, or universal joint, about the two perpendicular axes $X_4$ and $X_6$. These cardan joint kinematics efficiently reproduce the anatomical, saddle-type joint typically present between the metacarpal M and the trapezium T. Moreover, according to some embodiments, the first and second main surfaces 4 and 6 rest against the respective cortical bone layers of the metacarpal M and of the trapezium T, which helps prevent the body 2 from being forced into, or further penetrating one and/or the other of the metacarpal and trapezium bones M and T. By reducing the risk of this sinking effect of the implant 1 into bone, the mobility afforded by the implant 1 is longer lasting, and potentially lifelong in duration.

In some embodiments, in order to promote the rolling and sliding movements of the metacarpal M and of the trapezium T against the respective central parts 42 of the first and second main surfaces 4 and 6, the first and second, elliptic cross sections $S_4$ and $S_6$ of the first and second main surfaces 4 and 6 have, in the central regions 42 and 62, a smaller curvature than a remainder of the cross section. In other words, the central regions 42 and 62 of the first and second main surfaces 4 and 6 are more flattened relative to the surrounding portions of the implant 1, such as the peripheral regions 43 and 63, the central regions 42 and 62 being less curved than the rest of these surfaces. In some embodiments, the difference in curvature of the first and second cross sections $S_4$ and $S_6$ of the first and second main surfaces 4 and 6 between the central regions 42 and 62 and the peripheral regions 43 and 63 of the implant is relatively minor, while still having the desired effect.

In some embodiments, when in use, the body 2 is stabilized between the metacarpal M and the trapezium T on account of the elliptic curvature of the respective first and second cross sections $S_4$ and $S_6$ of the first and second main surfaces 4 and 6. In order to reinforce this stability, the first and second cross sections $S_4$ and $S_6$ of the respective peripheral regions 43 and 63 of the first and second main surfaces 4 and 6 have a greater curvature than the rest of the cross section. By exaggerating the curvature of the surfaces 4 and 6 in the area of their periphery, the surface cooperation of the body 2 with the metacarpal M and the trapezium T self-stabilizes the implant 1. Furthermore, the peripheral regions 43 and 63 of the surfaces 4 and 6 can thus compensate for the peripheral wear, associated with arthritis, of the mutually facing bone ends of the metacarpal M and trapezium T.

As shown, the body 2 is an implant of interposition. Thus, the thickness of the implant 1 along the axis Z-Z is limited, in the sense that the presence of the body 2 is adapted to avoid overstressing the trapeziometacarpal joint. Thus, in some embodiments, the maximum thickness $e_2$ of the body 2 (e.g., the thickness between the peripheral regions 43 and 63 of the first and second main surfaces 4 and 6), is less than 5 mm, and preferably equal to about 1 mm, although a variety of dimensions are contemplated. Similarly, in order to adapt optimally to the interosseous space between the metacarpal M and the trapezium T, the second main surface 6 has a dimension $L_6$, along its second axis $X_6$, that is greater than a dimension $L_4$ of the first main surface 4 along the first axis $X_4$.

The geometry of the first and second main surfaces 4 and 6 are optionally constructed with different shapes than described above. FIG. 6 is a diagram for visualizing a geometry of the first and second main surfaces 4 and 6 as shown in FIGS. 1 to 5. As shown in FIG. 6, the first and second main surfaces 4 and 6 correspond to profiles of axial segments, or portions, of cylinders defining the first and second axes $X_4$ and $X_6$, respectively. As shown, the axial segments have elliptical bases. In particular, the first and second cross sections $S_4$ and $S_6$ of the first and second main surfaces 4 and 6 have elliptic shapes centered on the first axis $X_4$ and second axis $X_6$, respectively. Thus, the geometric definition referenced above for the first and second main surfaces 4 and 6 is again shown here in a more schematic form.

FIGS. 7, 8 and 9 are diagrams similar to the one in FIG. 6 showing geometric variants of the first and second main surfaces 4 and 6 of the implant 1. In FIG. 7, first and second main surfaces 104 and 106, also described as metacarpal and trapezium joint surfaces, respectively, are represented, each of which correspond to a profile of an axial segment of a cylinder that is centered on first and second axes $X_{104}$ and $X_{106}$, respectively, and of which the first and second cross sections $S_{104}$ and $S_{106}$, respectively, are circular and centered on the aforementioned axes. In other words, in some embodiments, the first and second main surfaces 4 and 6 and the first and second main surfaces 104 and 106 differ only in terms of the geometric shape of their cross section, namely elliptical for the first and second main surfaces 4 and 6 and circular for the first and second main surfaces 104 and 106.

Similarly, in FIG. 8, first and second main surfaces 204 and 206, respectively, are represented, each of which corresponds to a profile of an axial segment of a cone that is centered on first and second axes $X_{204}$ and $X_{206}$, respectively, and of which the first and second cross sections $S_{204}$ and $S_{206}$, respectively, are circular. In yet another variant not depicted, the aforementioned first and second cross sections $S_{204}$ and $S_{206}$ are elliptic, rather than circular.

Likewise, in FIG. 9, first and second main surfaces 304 and 306, respectively, are represented, each of which corresponds to a profile of an axial segment of a torus that is associated with circular, central, first and second axes $X_{304}$ and $X_{306}$, respectively, and of which the first and second cross sections $S_{304}$ and $S_{306}$, respectively, that is to say the cross section in a plane perpendicular to the applicable axis, is circular and centered on the axes $X_{304}$ and $X_{306}$, respectively. In other variants not depicted, the first and second cross sections $S_{304}$ and $S_{306}$ of the aforementioned torus is made elliptical. Similarly, and once again in a variant not depicted, the circular cross section or the elliptical cross section of the torus, instead of being constant along the first and second axes $X_{304}$ and $X_{306}$, respectively, optionally increases or decreases along the first and second axes $X_{304}$ and $X_{306}$.

In still other embodiments, the curved geometry of the first and second cross sections $S_{104}$, $S_{106}$, $S_{204}$, $S_{206}$, $S_{304}$ and $S_{306}$ are continuously circular or elliptic or, by contrast, have substantial variations of curvature along their peripheries, for example. In particular, as has been mentioned above for the elliptic geometry of the first and second cross sections $S_4$ and $S_6$, the circular or elliptical geometry of the first and second cross sections $S_{104}$, $S_{106}$, $S_{204}$, $S_{206}$, $S_{304}$ and/or $S_{306}$ optionally have smaller curvatures in the central regions of the corresponding first and second main surfaces 104, 106, 204, 206, 304, and 306 and/or have a greater curvature in the peripheral regions of the first and second main surfaces 104, 106, 204, 206, 304, and 306 in relation to a remainder of the cross sections.

FIGS. 6 to 9 thus illustrate various design geometries of the metacarpal and trapezium joint surfaces, or first and second main surfaces of the implant 1, according to some various embodiments. Depending upon the application, the various design geometries provide desirable articular mobility simulating that of the natural trapeziometacarpal joint, once the body 2 is implanted, given that the two opposite first and second main surfaces 4 and 6, 104 and 106, 204 and 206, 304 and 306 of the implant 1 are arranged orthogonal to each other. In other words, the opposite first and second main surfaces 4 and 6, 104 and 106, 204 and 206, 304 and 306 of the implant 1 are arranged in such a way that their central, first and second axes $X_4$ and $X_6$, $X_{104}$ and $X_{106}$, $X_{204}$ and $X_{206}$, $X_{304}$ and $X_{306}$ extend substantially perpendicular to one another. In embodiments with surfaces having corresponding curved axes, such as the curved, first and second axes $X_{304}$ and $X_{306}$, the feature of perpendicularity between the particular set of opposing first and second main surfaces is exhibited via projection of the axes in the median plane $\pi$ of the body 2 of the implant 1, where the respective central regions of the first and second main surfaces 304 and 306 are arranged on either side of the plane $\pi$ (as is also the case with the projections on the plane $\pi$ of the rectilinear, first and second axes $X_4$ and $X_6$, $X_{104}$ and $X_{106}$, $X_{204}$ and $X_{206}$, which are also perpendicular to each other).

Figure 10:
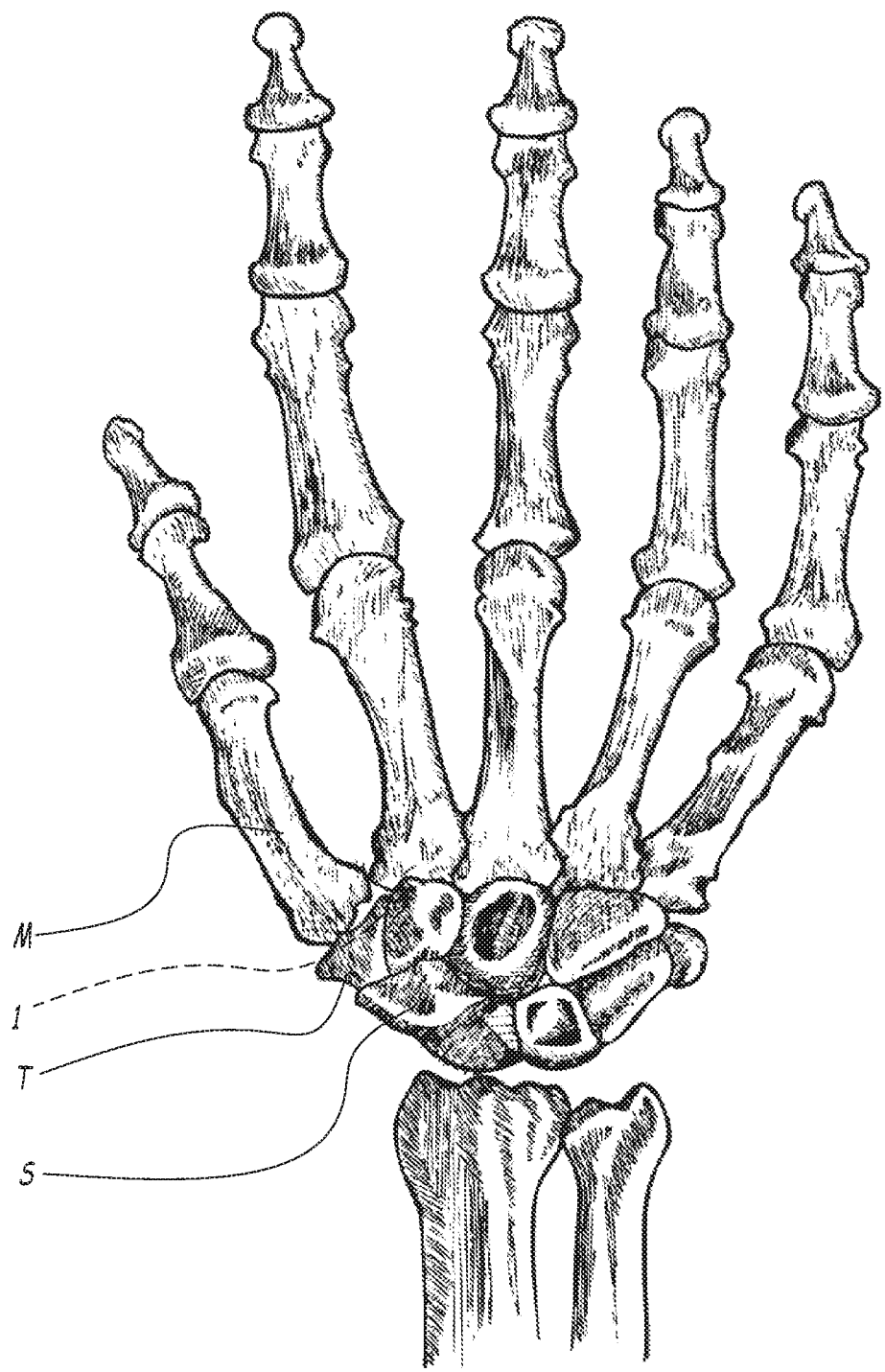
FIG. 10 is an elevation view showing some of the bone components of a right human hand, in which an implant according to the invention is to be implanted.
Figure 11:
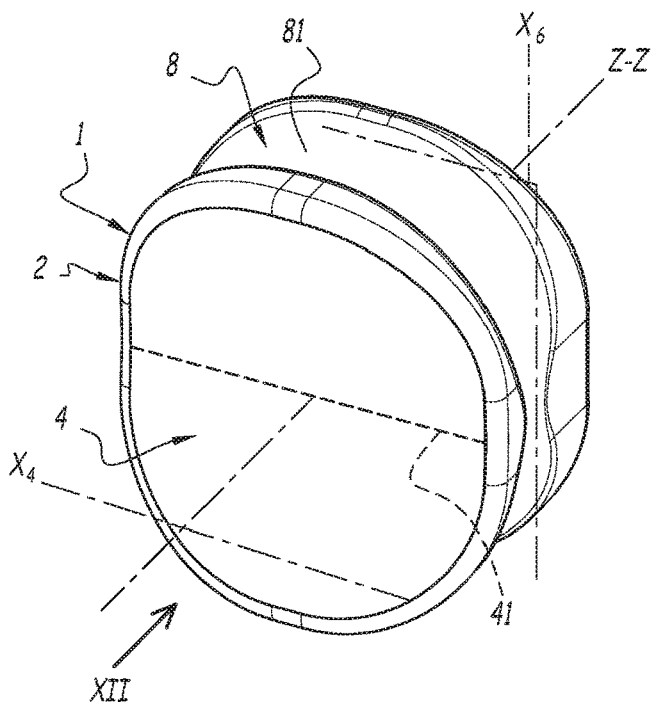
FIG. 11 is a perspective view of a trapezium interposition implant according to the invention.
Figure 12:
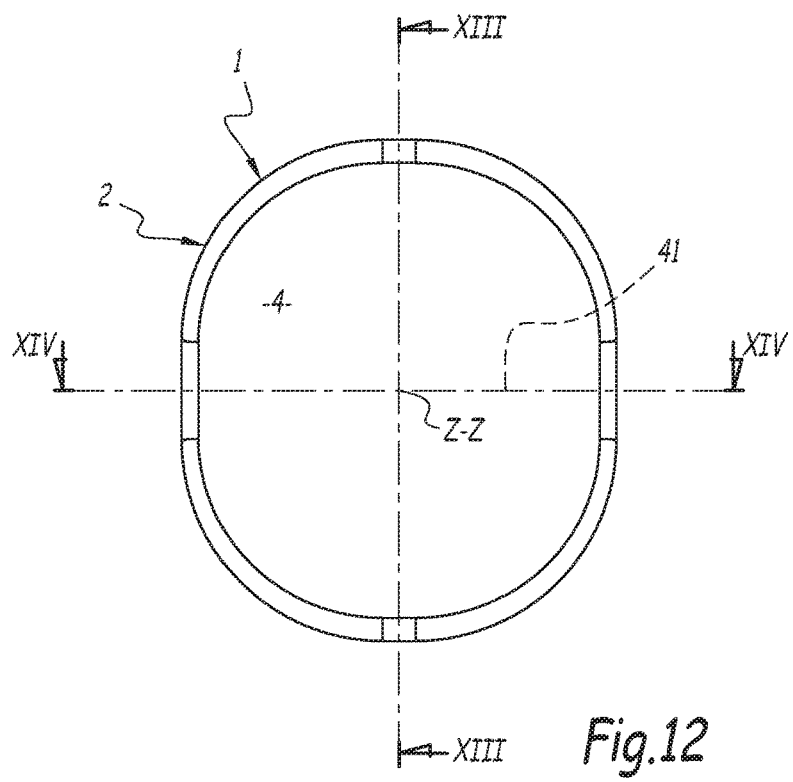
FIG. 12 is an elevation view along arrow XII of FIG. 11.

FIGS. 11 to 16 show an embodiment of a trapezium implant 1 according to the present invention which, as diagrammatically shown in dotted lines in FIG. 10, is suitable for being implanted by interposition between the scaphoid S and the first metacarpal M of a human hand, like that shown in FIG. 10 as an example.

The implant 1 includes a generally disk-shaped body 2, centered on a geometric axis referenced Z-Z. The body 2 thus delimits two opposite main surfaces 4 and 6 along the axis Z-Z, also referred to as metacarpal and scaphoid joint surfaces, respectively, or primary bone contact surfaces, for example. The main surfaces 4 and 6 are separated from each other by the thickness, along the axis Z-Z, of the body 2. A peripheral surface 8 connects the surfaces 4 and 6 to each other. The peripheral surface 8 extends about the entire periphery of the body 2 around the axis Z-Z, while having, in some embodiments, a thickness along axis Z-Z that is substantially constant.

As viewed along the axis Z-Z, the body 2 has a generally rectangular profile. In particular, in a cross section that is transverse to the axis Z-Z, the body 2 has a rectangular outer contour with rounded corners, although a variety of shapes are contemplated, including square, circular, elliptical, and others, for example.

In the embodiment shown in FIGS. 11 to 16, the implant 1 is formed as a single, unitary piece, consisting of the body 2 without extraneous components, such as a bone fixation component (for example, a screw) for anchoring the body 2 in the metacarpal M and the scaphoid S. For example, in some embodiments, the body 2 is secured in position via interposition between metacarpal M and the scaphoid S such that the body retains some freedom of movement to adapt its position to the stresses applied to it as a function of the movements of the hand, in particular the articulation movements between the implant and the bones of the metacarpal M and the scaphoid S.

In some embodiments, the body 2 is formed as a single piece of graphite covered with a layer of pyrolytic carbon, which provides good biocompatibility, high mechanical strength, and resists wearing of the metacarpal and the scaphoid. Although graphite and pyrolytic carbon have been referenced, other materials are contemplated, including metals such as chromium cobalt alloys, plastics, such as polyethylene, PEEK, and viscoelastic polymer materials, silicone, as well as ceramics and others.

Figure 13:
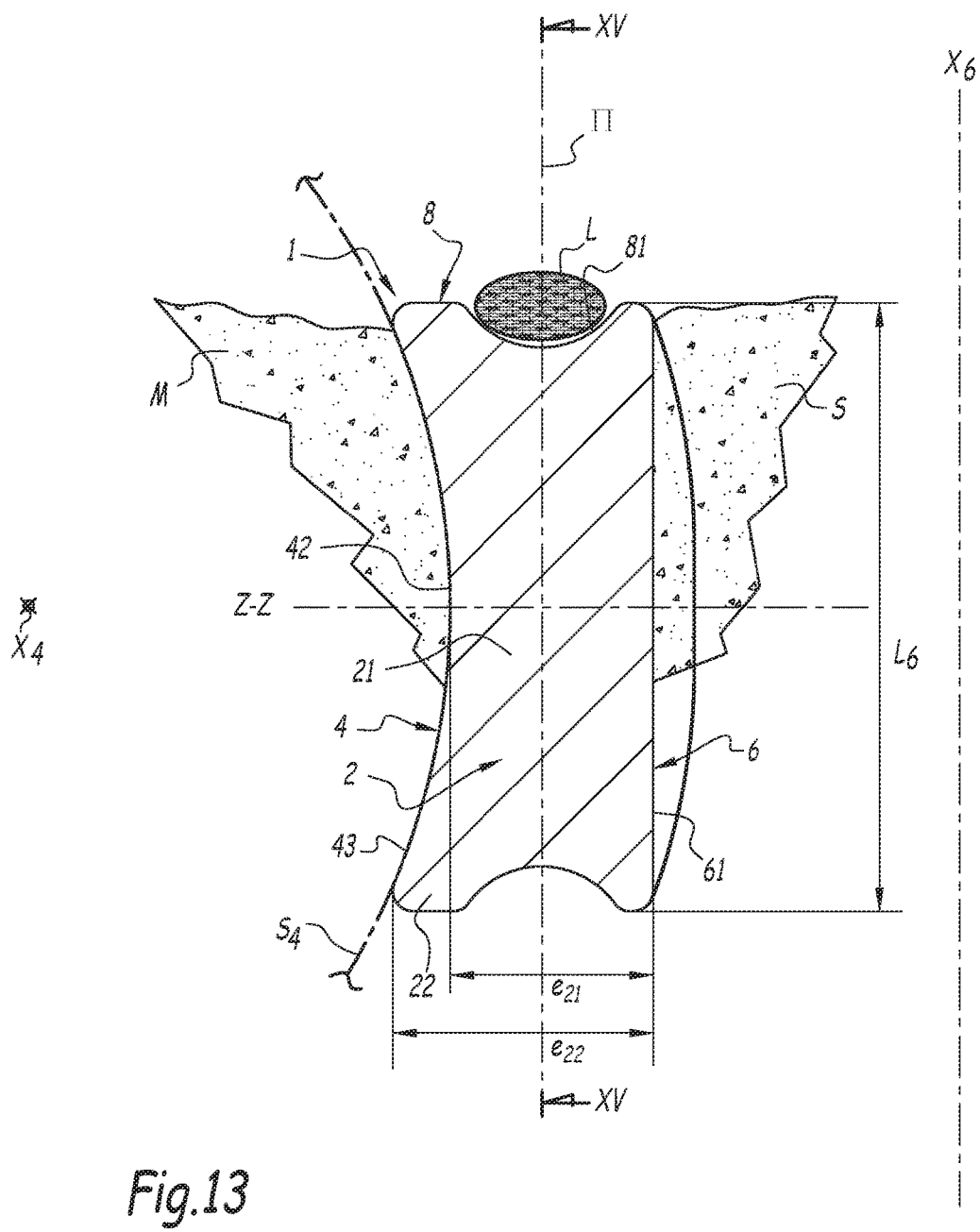
FIGS. 13 and 14 are cross-sectional views along lines XIII-XIII and XIV-XIV of FIG. 12, respectively, also partially showing the bones of the hand after placement of the implant.

As shown in FIG. 13, the first main surface 4 is concave and corresponds geometrically to a profile of an axial segment of a cylinder portion which is centered on a first axis $X_4$ and defines a first cross section $S_4$ that is substantially elliptical. In some embodiments, the first cross section $S_4$ is constant along the axis $X_4$ and corresponds to the base line of the surface 4. As shown, the first axis $X_4$ extends perpendicular to and intersects with the axis Z-Z (for reference, the first axis $X_4$ extends in and out of the page as depicted in FIG. 13).

Figure 14:
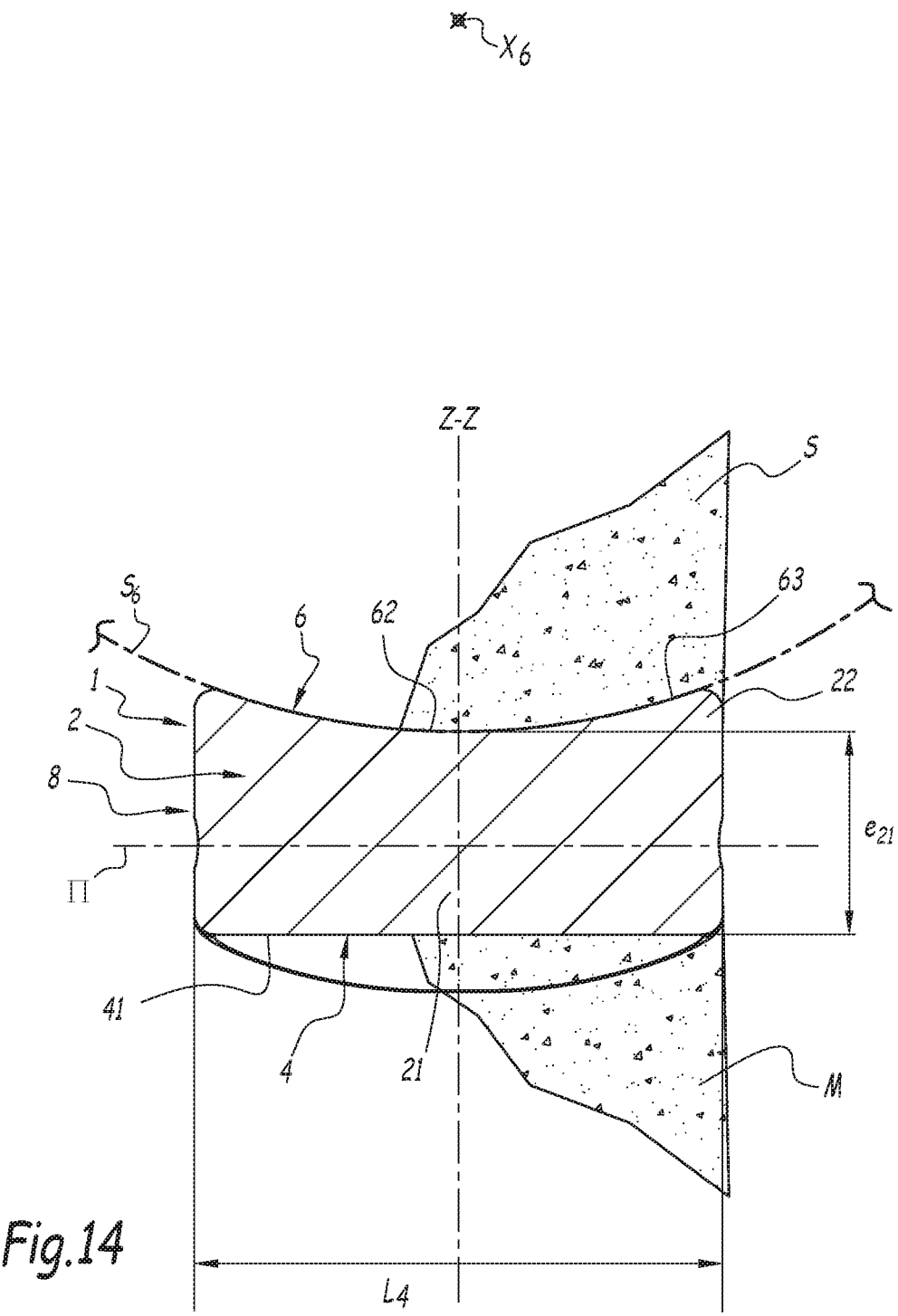
Figure 15:
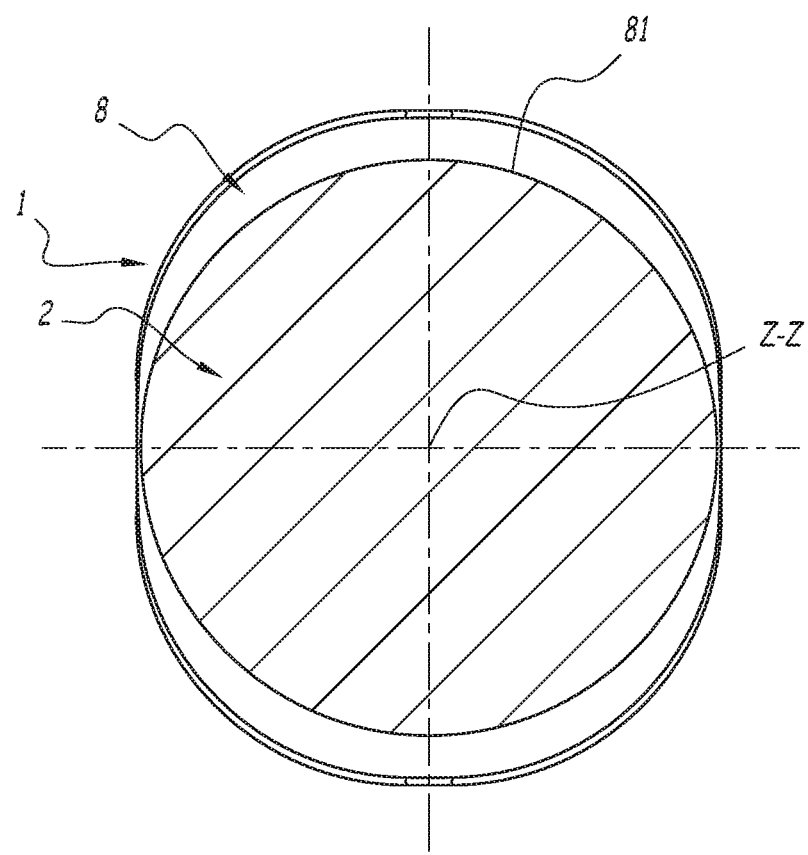
FIG. 15 is a cross-section along line XV-XV of FIG. 13.

As shown in FIG. 14, the second main surface 6 is concave and corresponds to a cylinder portion whose second cross section $S_6$ is substantially elliptical and is centered on a second axis $X_6$ that is perpendicular to and intersects with the axis Z-Z (for reference, the axis $X_6$ extends in and out of the page as depicted in FIG. 14).

Thus, as shown, the axes $X_4$ and $X_6$ extend perpendicular to each other and do not intersect. Base lines 41 (FIG. 14) and 61 (FIG. 13) belong respectively to the first and second main surfaces 4 and 6. Each of the base lines 41 and 61 extend parallel to the axes $X_4$ and $X_6$ and are perpendicular to each other. The base lines 41 and 61 are separated along the axis Z-Z by a central part 21 of the body 2. In other terms, in a median plane π of the body 2, which is perpendicular to the axis Z-Z and on either side of which the first and second main surfaces 4 and 6 are situated, the respective projections of the axes $X_4$ and $X_6$ are perpendicular and secant.

In some embodiments and as shown in FIGS. 13 and 14, in cross section through the axis Z-Z, the body 2 has a variable thickness, the thickness being at its minimum in the central part 21 of the body 2 and gradually increasing in the direction away from the central part 21 toward the peripheral part 22 of the body 2.

In some embodiments, the peripheral surface 8 defines a groove 81 (FIGS. 11 and 13) that runs lengthwise on the periphery of the body 2 around the axis Z-Z. In some embodiments, the depth of the groove 81 varies over the periphery of the body 2. The depth of the groove 81 may vary continuously between a maximum depth and a minimum depth The maximum depth may be disposed at two portions of the peripheral surface 8 that are opposite one another along the direction of the axis $X_6$ (see FIG. 13). The minimum depth may be disposed at two portions of the peripheral surface 8 that are opposite one another along the direction of the axis $X_4$ (see FIG. 14).

The following method of fitting the implant 1 in place between the metacarpal M and the scaphoid S is in accordance with some embodiments and is provided by way of example.

In some embodiments, in a first operating step, a surgeon accesses the trapezium T between the scaphoid S and the trapezium T via a posterior or anterior approach. To access the trapezium cavity between the metacarpal and the scaphoid, the capsular ligament and the ligaments surrounding that cavity are either preserved, by being retracted, or are partially incised, it being understood that the capsule and its ligaments will be reconstructed at the end of the intervention.

In some embodiments, in a second operating step, the surgeon performs a total trapeziectomy, using known surgical procedures, which will therefore not be further described. The surgeon thus frees the bone surfaces delimited by the metacarpal M and the scaphoid S which, previously, were pressed against the trapezium T. The surgeon can then prepare the metacarpal M if needed, in particular by cutting the crests and the dorsal and palmar banks of the head of the metacarpal M. For the scaphoid S, no preparation is performed. Furthermore, the surgeon may remove osteophytes from the surfaces of the metacarpal M and the scaphoid S.

In some embodiments, in a third operating step, tension may be applied between the metacarpal M and the scaphoid S in the longitudinal direction of the metacarpal M, and the surgeon positions the implant 1 in the trapezium cavity separating the metacarpal M and the scaphoid S. The surgeon interposes the body 2 between the metacarpal M and the scaphoid S such that the surface 4 faces the metacarpal M, with the axis $X_4$ extending in a frontal plane, and the surface 6 faces the scaphoid S, with the axis $X_6$ extending in an antero-posterior plane.

In a variant that is not shown, the implant 1 is fitted in place, between the metacarpal M and the scaphoid S, in a configuration tilted by 90 degrees about the axis Z-Z. In some embodiments, the ends of the metacarpal M and the scaphoid S are prepared before fitting the implant 1. Regardless, the body 2 is optionally implanted in such a manner that the first and second main surfaces 4 and 6 adapt better to the ends of the metacarpal M and scaphoid S of the patient being operated on, depending on the initial state of these bone ends, and/or to minimize a depth to which the bone ends are cut during preparation.

Once the implant 1 has been positioned, or interposed, between the metacarpal M and the scaphoid S, the tension previously applied to the metacarpal M and the scaphoid S is released such that the capsule and the ligaments surrounding the trapezium cavity move the metacarpal M and the scaphoid S toward each other. In some embodiments, the body 2 of the implant 1 and/or the metacarpal M and the scaphoid S are adapted such that the implant 1 is movably held between the metacarpal M and the scaphoid S, under the stress provided by the capsule and the ligaments surrounding the trapezium cavity. In other words, the capsule and the ligaments provide a stress whose resultant force, or a substantial component thereof, is substantially aligned with the axis Z-Z.

The surgeon then closes the tissue around the implant 1 by, for example, reconstruction or using ligamentoplasty. In some embodiments, ligamentoplasty may make use of the peripheral groove 81. Specifically, the surgeon partially cinches the body 2 with a tendon that is part of or connected to the surrounding tissues. In some embodiments, the tendon is a tendinous tongue extending from the radial flexor muscle of the carpus, commonly referred to as the "FCR" (flexor carpi radialis). The tongue extends from the back of the thumb and is fastened at the palmar base of the capsule surrounding the trapezium cavity. Therebetween, the tongue is positioned so as to extend around at least a portion of the body 2 of the implant 1. In some embodiments, the tendon is a tendinous tongue extending from the long abductor muscle of the thumb, commonly referred to as the "APL" (abductor pollisis longus) muscle. The tongue extends from the palmar base of the thumb and is attached to the dorsal side of the capsule. Therebetween, the tongue is positioned so as to extend around at least a portion of the body 2 of the implant 1. For example, as shown in FIG. 13, one of the above tendinous tongues, or another tendon, is identified using reference L. The tongue L is slidingly received in one of the maximum-depth portions of the peripheral groove 81. In some embodiments, the presence of the tendon L, or other tissues, facilitates stability of the implant 1 in the trapezium cavity. In some embodiments, the tendon L or tissue is disposed within the peripheral groove 81 on the anterior outer edge of the implant 1. In some embodiments, during movements of the thumb, the tendon L or tissue slides, in the longitudinal direction of the tendon L or tissue, relative to the implant 1 within the peripheral groove 81.

The thumb thus fitted with the implant 1 exhibits a kinematic behavior that is similar to, or even nearly identical to the natural anatomical behavior facilitated by the trapezium. For example, the implant 1 is configured such that the metacarpal M articulates against the first main surface 4 by tilting about the first axis $X_4$, whereas the scaphoid S articulates against the surface 6 by tilting about the second axis $X_6$. By virtue of the implant 1, the metacarpal M and the scaphoid S are articulated with respect to each other in the manner of a cardan joint, or universal joint, about the two perpendicular axes $X_4$ and $X_6$. These cardan joint kinematics effectively reproduce the mobility of the substantially saddle-like natural articulations between the metacarpal and the trapezium and between the trapezium and the scaphoid. Furthermore, according to some embodiments, the first and second main surfaces 4 and 6 rest against the respective bone cortical layers of the metacarpal M and the scaphoid S, which helps prevent the body 2 from being forced into, or penetrating the metacarpal M and the scaphoid S. By reducing the risk of this sinking effect of the implant 1 into the bones, the mobility facilitated by the implant 1 is longer lasting, and potentially lifelong in duration.

In some embodiments, in order to promote the rolling and sliding movements of the metacarpal M and the scaphoid S against the respective central parts 42 and 62 of the first and second main surfaces 4 and 6, the respective elliptical cross sections $S_4$ and $S_6$ of the first and second main surfaces 4 and 6 have, in the central regions 42 and 62, a smaller curvature than the remainder of the cross section. In other words, the central regions 42 and 62 of the first and second main surfaces 4 and 6 are more flattened relative to the surrounding portions of the implant 1, such as the peripheral regions 43 and 63.

In some embodiments, during use, the body 2 is stabilized between the metacarpal M and the scaphoid S due to the elliptical curvature of the respective first and second sections $S_4$ and $S_6$ of the first and second main surfaces 4 and 6. In order to reinforce this stability, the first and second sections $S_4$ and $S_6$ of the respective peripheral regions 43 and 63 of the first and second main surfaces 4 and 6 have a greater curvature than the remainder of the cross section. By exaggerating the curvature of the first and second main surfaces 4 and 6 in the area of their periphery, the surface cooperation of the body 2 with the metacarpal M and the scaphoid S self-stabilizes the implant 1. Furthermore, the peripheral regions 43 and 63 of the first and second main surfaces 4 and 6 can thus compensate for peripheral wear, associated with arthritis, of the bone ends of the metacarpal M and the scaphoid S.

As shown, the body 2 is a trapezium implant. Thus, the thickness of the implant 1 along the axis Z-Z is limited, in the sense that the presence of the body 2 is adapted to maintain sufficient separation between the metacarpal M and the scaphoid S without hyper-stressing the trapezium cavity. Thus, in some embodiments, the minimum thickness $e_{21}$ of the body 2 (e.g., the thickness in the central region 21 between the central regions 42 and 62 of the first and second main surfaces 4 and 6), is greater than or equal to 5 mm, although a variety of dimensions are contemplated. In some embodiments, the maximum thickness $e_{22}$ of the body 2 (e.g., the thickness in the peripheral part 22 between the peripheral regions 43 and 63 of the first and second main surfaces 4 and 6), is less than 15 mm, although a variety of dimensions are contemplated. Similarly, in order to adapt to the trapezium cavity between the metacarpal M and the scaphoid S, the second main surface 6 has a dimension $L_6$, along the second axis $X_6$, that is greater than a dimension $L_4$ of the first main surface 4 along the first axis $X_4$.

The geometry of the first and second main surfaces 4 and 6 may be constructed with different shapes than those described above. FIG. 16 shows a diagram for visualizing a geometry of the first and second main surfaces 4 and 6 as shown in FIGS. 11 to 15. As shown in FIG. 16, the first and second main surfaces 4 and 6 correspond to profiles of axial segments, or portions, of cylinders defining the axes $X_4$ and $X_6$, respectively. As shown, the axial segments have elliptical bases. In particular, the first and second cross sections $S_4$ and $S_6$ of the first and second main surfaces 4 and 6 have elliptical shapes centered on the first axis $X_4$ and the second axis $X_6$, respectively. Thus, the geometric definition referenced above for the first and second main surfaces 4 and 6 is again shown here in a more schematic form.

FIGS. 17-19 are diagrams similar to that of FIG. 16 showing geometric variants of the first and second main surfaces 4 and 6 of the implant 1. In FIG. 17, the first and second main surfaces 4 and 6, also described as metacarpal and scaphoid articular surfaces, respectively, are represented, each of which correspond to a profile of an axial segment of the cylinder that is centered on first and second axes $X_{104}$ and $X_{106}$, respectively, and of which the first and second cross sections $S_{104}$ and $S_{106}$, respectively, are circular and centered on the aforementioned axes. In other words, in some embodiments, the first and second main surfaces 4 and 6 and the first and second main surfaces 104 and 106 differ only in terms of the geometric shape of their cross section, namely, elliptical for the first and second main surfaces 4 and 6 and circular for the first and second main surfaces 104 and 106. Similarly, in FIG. 18, the first and second main surfaces 204 and 206, respectively, are represented, each of which corresponds to a profile of an axial segment of a cone that is centered on first and second axes $X_{204}$ and $X_{206}$, respectively, and of which the first and second cross sections $S_{204}$ and $S_{206}$, respectively, are circular. In yet another variant not depicted, the aforementioned first and second cross sections $S_{204}$, $S_{206}$ are elliptical, rather than circular.

Likewise, in FIG. 19, the first and second main surfaces 304 and 306, respectively, are represented, each of which corresponds to a profile an axial segment of a torus that is associated with circular, central, first and second axes $X_{304}$ and $X_{306}$, respectively, and of which the first and second cross sections $S_{304}$ and $S_{306}$, respectively, (that is, the cross section in a plane perpendicular to the applicable axis) are circular and centered on the axes $X_{304}$ and $X_{306}$, respectively. In other variants not depicted, the first and second cross sections $S_{304}$ and $S_{306}$ of the aforementioned torus is elliptical. Similarly, and once again in a variant not depicted, the circular cross section or the elliptical cross section of the torus, instead of being constant along the first and second axes $X_{304}$ and $X_{306}$, respectively, optionally increases or decreases along the first and second axes $X_{304}$ and $X_{306}$.

In still other embodiments, the curved geometry of the first and second cross sections $S_{104}$, $S_{106}$, $S_{204}$, $S_{206}$, $S_{304}$ and $S_{306}$ are continuously circular or elliptical or, by contrast, have substantial curvature variations along their peripheries, for example. In particular, as has been mentioned above for the elliptical geometry of the first and second cross sections $S_4$ and $S_6$, the circular or elliptical geometry of the first and second cross sections $S_{104}$, $S_{106}$, $S_{204}$, $S_{206}$, $S_{304}$ and/or $S_{306}$ may have smaller curvatures in the central region of the corresponding first and second main surfaces 104, 106, 204, 206, 304, 306 and/or have a greater curvature in the peripheral regions of the first and second main surfaces 104, 106, 204, 206, 304, and 306 in relation to a remainder of the cross sections.

FIGS. 16 to 19 thus illustrate various design geometries of the metacarpal and scaphoid joint surfaces of the implant 1, according to some embodiments. Depending upon the application, the various design geometries provide articular mobility simulating the natural mobility facilitated by the trapezium, once the body 2 is implanted, given that the two opposite first and second main surfaces 4 and 6, 104 and 106, 204 and 206, and 304 and 306 of the implant 1 are arranged orthogonally to each other. In other words, the first and second main surfaces 4 and 6, 104 and 106, 204 and 206, 304 and 306 of the implant 1 are arranged in such a way that their central, first and second axes $X_4$ and $X_6$, $X_{104}$ and $X_{106}$, $X_{204}$ and $X_{206}$, and $X_{304}$ and $X_{306}$ extend substantially perpendicular to one another. In embodiments with surfaces having corresponding curved axes, such as the curved, first and second axes $X_{304}$ and $X_{306}$, the feature of perpendicularity between the particular set of opposing first and second main surfaces is exhibited via projection of the axes in the median plane π of the body 2 of the implant 1, where the respective central regions of the first and second main surfaces 304 and 306 are arranged on either side of the plane π (as is also the case with the projections on the plane π of the rectilinear, first and second axes $X_4$ and $X_6$, $X_{104}$ and $X_{106}$, $X_{204}$ and $X_{206}$, which are also perpendicular to each other).

Various modifications and additions can be made to the exemplary embodiments discussed without departing from the scope of the present invention. For example, although various embodiments have been described with similar, angularly offset shapes for the various first and second main surfaces, it is also contemplated that the design geometry of the first main surface is the same as, with strictly identical or different dimensioning, or different than, the design geometry chosen for the second main surface of the implant. Additionally, while the embodiments described above refer to particular features, the scope of this invention also includes embodiments having different combinations of features and embodiments that do not include all of the above described features.

The following is claimed:

1. A method for coupling a first bone of a hand of a patient to a second bone of the hand of the patient, the method comprising:
    providing an implant comprising a body defining:
    a median plane;
    a first joint surface having a first central region adapted to articulate with the first bone;
    a second joint surface having a second central region adapted to articulate with the second bone, the second central region being disposed on an opposite side of the median plane of the body relative to the first central region, wherein the first central region and the second central region correspond to profiles of a first axial segment and a second axial segment, respectively, the first and second axial segments being each one of a cylinder, a cone and a torus and being centered on a first axis and a second axis, respectively, the first and second axes, as projected on the median plane, being substantially perpendicular to each other; and
    a peripheral surface connecting the first joint surface and the second joint surface, the peripheral surface defining a peripheral groove;
    forming a cavity between the first bone and the second bone;
    interposing the implant between the first bone and the second bone in the cavity such that the first joint surface of the implant comes into direct contact and articulates with the first bone and the second joint surface of the implant comes into direct contact and articulates with the second bone; and
    cinching the body of the implant with a tendon of the hand of the patient, the tendon being slidably received in the peripheral groove of the implant.

2. The method of claim 1, wherein upon cinching the body of the implant with the tendon, the tendon is received only in a portion of the peripheral groove.

3. The method of claim 1, wherein the peripheral groove has a depth which varies over the peripheral surface of the body, and wherein upon cinching the body of the implant with the tendon, the tendon is received in a maximum-depth portion of the peripheral groove.

4. The method of claim 1, wherein the implant is interposed between the first bone and the second bone in the cavity such that the first bone is free to articulate against the first joint surface by tilting about the first axis and the second bone is free to concurrently articulate against the second joint surface by tilting about the second axis.

5. The method of claim 1, wherein the implant is interposed between the first bone and the second bone in the cavity such that the first central region of the first joint surface of the implant comes into direct contact and articulates with the first bone and the second central region of the second joint surface of the implant comes into direct contact and articulates with the second bone.

6. The method of claim 1, wherein the first bone is a first metacarpal and the second bone is a scaphoid, wherein the first joint surface is a metacarpal joint surface which comes into direct contact and articulates with the first metacarpal upon interposing the implant between the first metacarpal and the scaphoid in the cavity, and wherein the second joint surface is a scaphoid joint surface which comes into contact and articulates with the scaphoid upon interposing the implant between the first metacarpal and the scaphoid in the cavity.

7. The method of claim 6, wherein the cavity between the first metacarpal and the scaphoid is trapezium and is formed by performing a total trapeziectomy.

8. The method of claim 6, wherein upon interposing the implant between the first metacarpal and the scaphoid in the cavity, the implant is oriented in the cavity such that the first axis of the implant extends in a frontal plane of the patient and the second axis of the implant extends in an anteroposterior plane of the patient.

9. The method of claim 8, wherein the peripheral groove of the implant has a depth which varies continuously between a maximum depth and a minimum depth, the maximum depth being disposed at two portions of the peripheral surface of the implant that are opposite one another along the direction of the second axis, and the minimum depth being disposed at two portions of the peripheral surface that are opposite one another along the direction of the first axis, and wherein upon cinching the body of the implant with the tendon, the tendon is received in one of the two maximum-depth portions of the peripheral groove.

10. The method of claim 6, wherein upon interposing the implant between the first metacarpal and the scaphoid in the cavity, the implant is oriented in the cavity such that the first axis of the implant extends in an anteroposterior plane of the patient and the second axis of the implant extends in a frontal plane of the patient.

11. The method of claim 6, the tendon is a tendinous tongue extending from the radial flexor muscle of the carpus of the hand of the patient.

12. The method of claim 6, the tendon is tendinous tongue extending from the long abductor muscle of the thumb of the hand of the patient.

13. A method for coupling a first metacarpal of a hand of a patient to a scaphoid of the hand of the patient, the method comprising:
   providing an implant comprising a body defining:
      a median plane;
      a metacarpal joint surface having a first central region adapted to articulate with the first metacarpal; and
      a scaphoid joint surface having a second central region adapted to articulate with the scaphoid, the second central region being disposed on an opposite side of the median plane of the body relative to the first central region, wherein the first central region and the second central region correspond to profiles of a first axial segment and a second axial segment, respectively, the first and second axial segments being each one of a cylinder, a cone and a torus and being centered on a first axis and a second axis, respectively, the first and second axes, as projected on the median plane, being substantially perpendicular to each other;
   forming a trapezium cavity between the first metacarpal and the scaphoid by performing a total trapeziectomy; and
   interposing the implant between the first metacarpal and the scaphoid in the trapezium cavity such that the metacarpal joint surface of the implant comes into direct contact and articulates by tilting about the first axis with the first metacarpal, with the first axis of the implant extending in one of frontal and anteroposterior planes of the patient, and the scaphoid joint surface of the implant comes into direct contact and articulates by tilting about the second axis with the scaphoid, with the second axis of the implant extending in the other of the frontal and anteroposterior planes.

14. The method of claim 13, wherein respective bone cortical layers of the first metacarpal and the scaphoid are not removed before interposing the implant between said bone cortical layers of the first metacarpal and the scaphoid in the trapezium cavity.

15. The method of claim 13, wherein upon interposing the implant between the first metacarpal and the scaphoid in the trapezium cavity, a tensile force is applied in a longitudinal direction of the first metacarpal, then the implant is positioned in the trapezium cavity, and then the tensile force is released to secure the implant between the first metacarpal and the scaphoid.

16. The method of claim 13, wherein upon interposing the implant between the first metacarpal and the scaphoid in the trapezium area, the implant separates the first metacarpal and the scaphoid by a thickness of less than 5 mm.

17. The method of claim 13, wherein after interposing the implant between the first metacarpal and the scaphoid in the trapezium cavity, the body of the implant is not anchored in the first metacarpal and the scaphoid so as to retain freedom of movement in use.

* * * * *